United States Patent
Duane et al.

(10) Patent No.: US 6,800,065 B2
(45) Date of Patent: Oct. 5, 2004

(54) CATHETER AND GUIDE WIRE EXCHANGE SYSTEM

(75) Inventors: Patrick J. Duane, Galway (IE); Gerry Clarke, Galway (IE); Niall Duffy, Galway (IE); Noel Coyle, Galway (IE); John MacNamara, Galway (IE); David Quinn, Galway (IE); Declan Costello, Galway (IE); Robert Murray, Santa Rosa, CA (US); Ashish Varma, Galway (IE); Patrick J. Carmody, Galway (IE)

(73) Assignee: Medtronic AVE, Inc., Santa Rosa, CA (US)

( * ) Notice: Subject to any disclaimer, the term of this patent is extended or adjusted under 35 U.S.C. 154(b) by 150 days.

(21) Appl. No.: 10/116,234

(22) Filed: Apr. 4, 2002

(65) Prior Publication Data

US 2003/0191491 A1 Oct. 9, 2003

(51) Int. Cl.$^7$ ............................................... A61M 29/00
(52) U.S. Cl. .................................................. 604/96.01
(58) Field of Search ............................... 606/191–198; 604/96.01, 97.01; 600/434, 585

(56) References Cited

U.S. PATENT DOCUMENTS

| | | |
|---|---|---|
| 4,748,982 A | 6/1988 | Horzewski et al. |
| 4,762,129 A | 8/1988 | Bonzel |
| 4,988,356 A | 1/1991 | Crittenden et al. |
| 5,040,548 A | 8/1991 | Yock |
| 5,061,273 A | 10/1991 | Yock |
| 5,171,222 A | 12/1992 | Euteneuer et al. |
| 5,205,822 A | 4/1993 | Johnson et al. |
| 5,263,932 A | 11/1993 | Jang |
| 5,290,241 A | 3/1994 | Kraus et al. |
| 5,300,085 A | 4/1994 | Yock |
| 5,324,269 A | 6/1994 | Miraki |
| 5,334,187 A | 8/1994 | Fishcell et al. |
| 5,350,395 A | 9/1994 | Yock |
| 5,357,978 A | 10/1994 | Turk |
| 5,387,226 A | 2/1995 | Miraki |
| 5,389,087 A | 2/1995 | Miraki |
| 5,409,459 A | 4/1995 | Gambale |
| 5,451,233 A | 9/1995 | Yock |
| 5,458,639 A | 10/1995 | Tsukashima et al. |
| 5,460,185 A | 10/1995 | Johnson et al. |
| 5,496,346 A | 3/1996 | Horzewski et al. |
| 5,501,227 A | 3/1996 | Yock |
| 5,533,968 A * | 7/1996 | Muni et al. .................. 606/194 |
| 5,549,556 A | 8/1996 | Ndondo-Lay et al. |
| 5,571,094 A | 11/1996 | Sirhan |
| 5,578,009 A | 11/1996 | Kraus et al. |
| 5,626,600 A | 5/1997 | Horzewski et al. |
| 5,685,312 A | 11/1997 | Yock |
| 5,718,680 A | 2/1998 | Kraus et al. |
| 5,749,888 A | 5/1998 | Yock |
| 5,769,868 A | 6/1998 | Yock |
| 5,868,706 A | 2/1999 | Cox |
| 5,919,175 A | 7/1999 | Sirhan |
| 5,947,925 A | 9/1999 | Ashiya et al. |
| 6,036,715 A | 3/2000 | Yock |
| 6,096,009 A | 8/2000 | Windheuser et al. |
| RE36,857 E | 9/2000 | Euteneuer et al. |
| 6,165,197 A | 12/2000 | Yock |
| 6,193,686 B1 * | 2/2001 | Estrada et al. ........... 604/96.01 |
| 6,196,995 B1 | 3/2001 | Fagan |
| 6,322,577 B1 | 11/2001 | Mcinnes et al. |

* cited by examiner

*Primary Examiner*—Kevin T. Truong
(74) *Attorney, Agent, or Firm*—Catherine C. Maresh; James F. Crittenden

(57) ABSTRACT

A catheter and guide wire exchange system including a catheter having a guide wire lumen with a guide way extending along the length of a stiffened proximal shaft portion, and a guide member slidably disposed about the proximal shaft for directing a guide wire into or out of the guide way and the guide wire lumen. The guide member may be slid along the proximal shaft portion and the guide wire in zipper-like fashion so that the guide wire is contained within the guide wire lumen distal to the guide member and with the guide wire and catheter being separated proximal of the guide member.

23 Claims, 7 Drawing Sheets

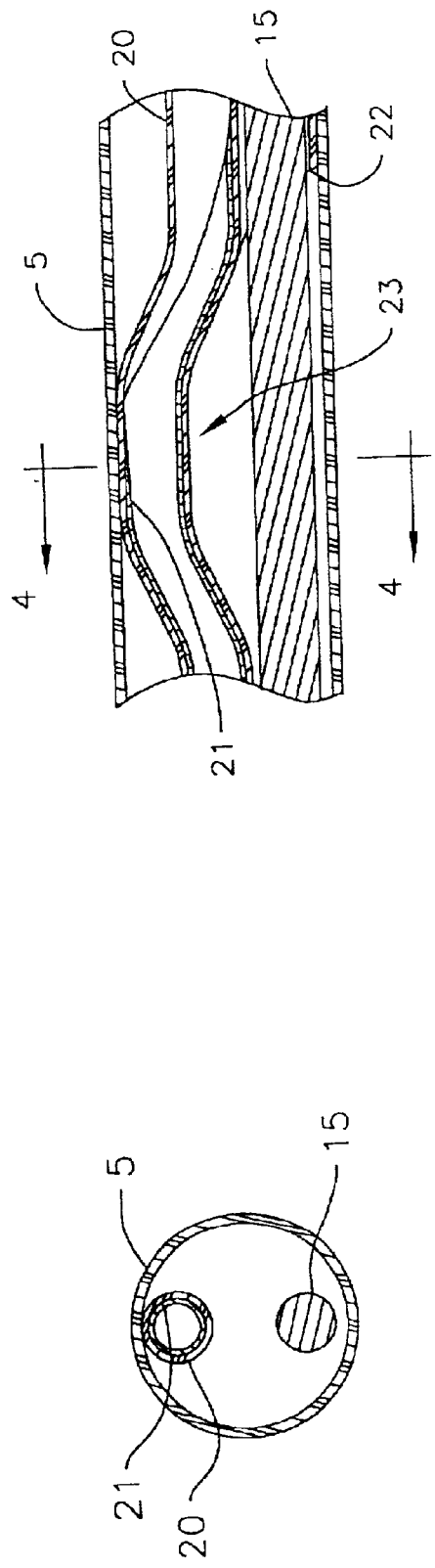
FIG. 3 (PRIOR ART)
FIG. 4 (PRIOR ART)
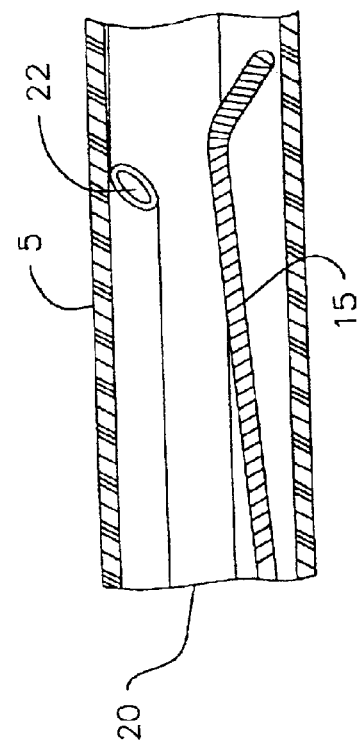
FIG. 5 (PRIOR ART)

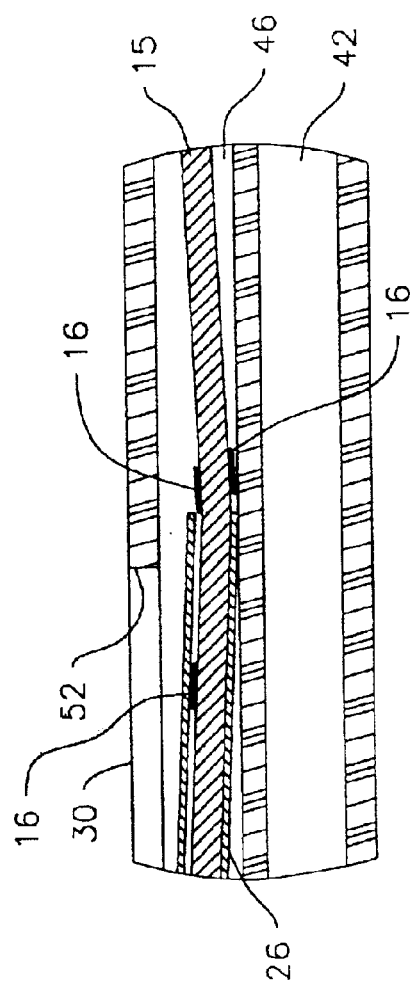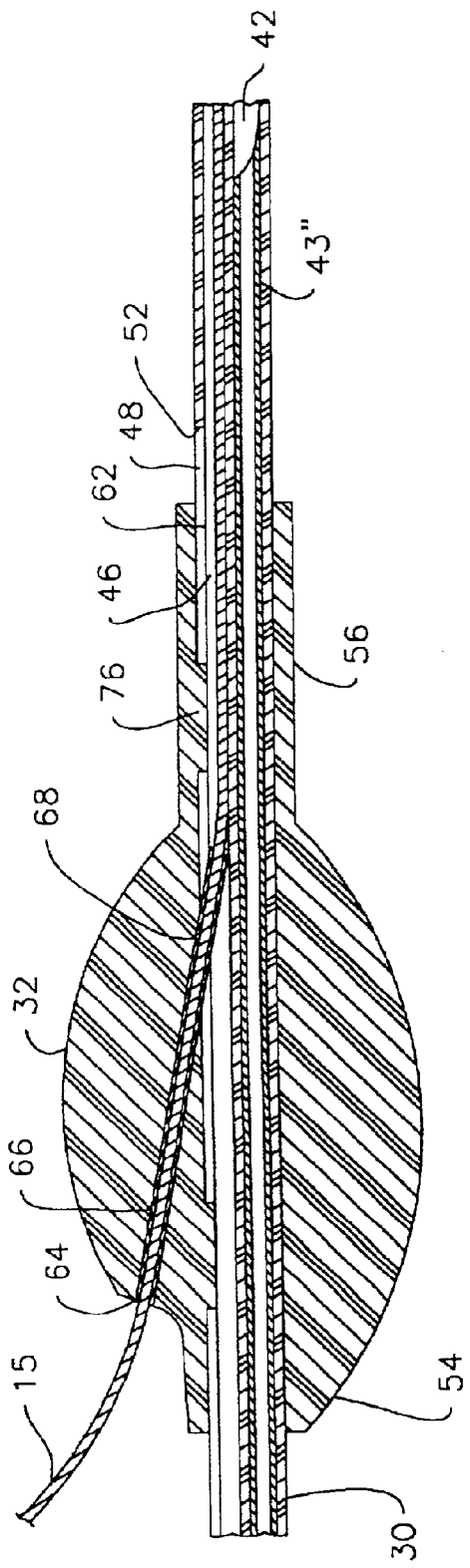

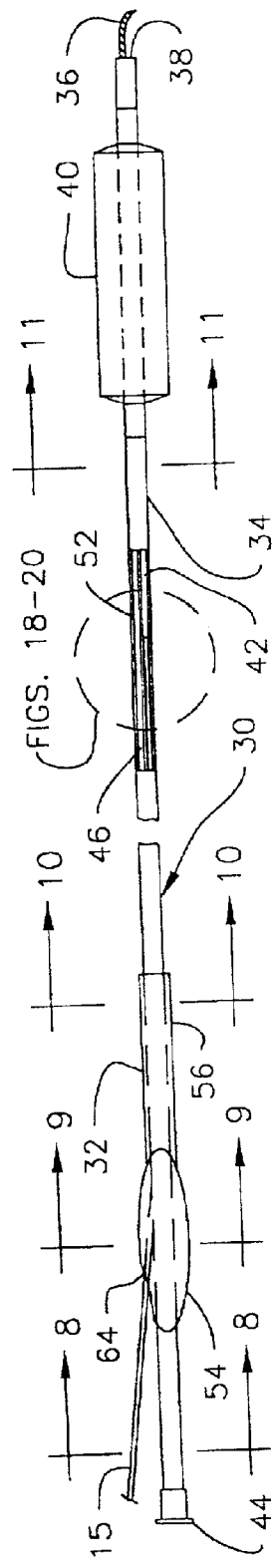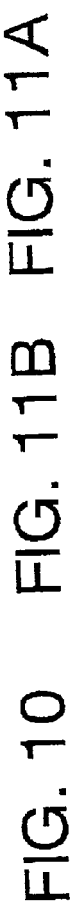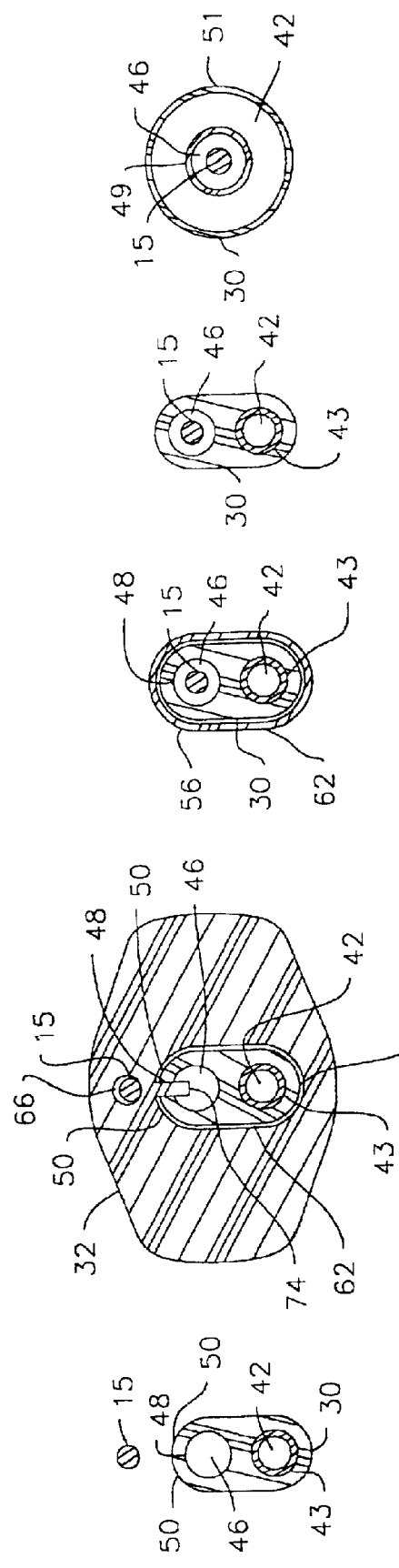

CATHETER AND GUIDE WIRE EXCHANGE SYSTEM

FIELD OF THE INVENTION

The present invention relates to catheters used with guide wires in the cardiovascular system and, in particular, to a system for facilitating exchange of such catheters and guide wires, and for transporting such catheters and guide wires to selected sites within a patient.

BACKGROUND OF THE INVENTION

Catheters are inserted to various locations within a patient for a wide variety of purposes and medical procedures. For example only, one type of catheter is used in percutaneous catheter intervention (PCI) for the treatment of a vascular constriction termed a stenosis. In this instance, the catheter has a distally mounted balloon that can be placed, in a deflated condition, within the stenosis, and then inflated to dilate the narrowed lumen of the blood vessel. Such balloon dilation therapy is generally named percutaneous translumi-nal angioplasty (PTA). The designation PTCA, for percutaneous transluminal coronary angioplasty, is used when the treatment is more specifically employed in vessels of the heart. PTCA is used to open coronary arteries that have been occluded by a build-up of cholesterol fats or atherosclerotic plaque. The balloon at the distal end of the catheter is inflated, causing the site of the stenosis to widen.

The dilation of the occlusion, however, can form flaps, fissures and dissections, which may result in reclosure of the dilated vessel or even perforations in the vessel wall. Implantation of a stent can provide support for such flaps and dissections and thereby prevent reclosure of the vessel or provide a patch repair for a perforated vessel wall until corrective surgery can be performed. A stent is typically a cylindrically shaped device formed from wire(s) or a metal tube and is intended to act as a permanent prosthesis. A stent is deployed in a body lumen from a radially compressed configuration into a radially expanded configuration that allows it to contact and support a body lumen. A stent can be implanted during an angioplasty procedure by using a balloon catheter bearing a compressed stent that has been loaded onto the balloon. The stent radially expands as the balloon is inflated, forcing the stent into contact with the body lumen, thereby forming a supporting relationship with the lumen walls. Alternatively, self-expanding stents may be deployed with a sheath-based delivery catheter. Deployment is effected after the stent has been introduced percutaneously, transported transluminally and positioned at a desired location by the delivery catheter. In addition to angioplasty and stenting procedures, other therapeutic procedures require use of a delivery catheter, such as drug delivery, filters, occlusion devices, diagnostic devices and radiation treatment.

Typically, the placement of such therapeutic delivery catheters involves the use of a guide wire, which maybe inserted into the patient's vasculature through the skin, and advanced to the location of the treatment site. The delivery catheter, which has a lumen adapted to receive the guide wire, then is advanced over the guide wire. Alternatively, the guide wire and the delivery catheter may be advanced together, with the guide wire protruding from the distal end of the delivery catheter. In either case, the guide wire serves to guide the delivery catheter to the location to be treated.

To treat small diameter vessels remote from the entry point into the patient, a guiding catheter is used to span the distance. For example, in PTCA or stent delivery, a guiding catheter is typically inserted into a large artery near the patient's groin, and then advanced toward the heart to the entry opening, or ostium, of the diseased coronary artery. The guiding catheter provides a tubular conduit through which catheters and guide wires can be passed from outside the patient to the vessel being treated.

There are three general types of catheters: "over-the-wire" (OTW) catheters, "rapid exchange" (RX) or single operator catheters and "fixed wire" (FW) or "a balloon on a wire" catheters. An over-the-wire catheter comprises a guide wire lumen that extends the entire length of the catheter. The guide wire is disposed entirely within the catheter guide wire lumen except for the distal and proximal portions of the guide wire, which extend beyond the distal and proximal ends of the catheter respectively. An OTW catheter typically has a "co-axial" catheter construction, wherein two hollow tubes and are nested together such that the lumen 17 of the inner tube can slidably receive guide wires and the annular luminal space 19 formed between the inner and outer tubes is used for inflation/deflation fluid, as shown in FIGS. 1A and 2A. An alternative "multilumen" OTW catheter construction has an elongate shaft made from a single extruded tube having two lumens 17' and 19' formed side-by-side, as shown in FIGS. 1B and 2B. OTW catheters that contain both multilumen segments and coaxial segments are also known.

Over-the-wire catheters have many advantages traceable to the presence of a full-length guide wire lumen such as good stiffness and pushability for readily advancing the catheter through the tortuous vasculature and across tight stenoses. The full-length guide wire lumen is also available for transporting radiocontrast dye to the stenosed artery, for making pressure measurements, for infusing drugs and for other therapies. Finally, the full-length guide wire lumen permits removal and replacement of a guide wire in an indwelling catheter, as may be required to alter the shape of the guide wire tip. It is also sometimes desirable to exchange one guide wire for another guide wire having a different stiffness. For example, a relatively soft, or flexible guide wire may prove to be suitable for guiding a PTCA catheter through a particularly tortuous anatomy, whereas following up with a stent-delivery catheter through the same vasculature region may require a guide wire that is relatively stiffer.

Over-the-wire catheters do suffer some shortcomings, however. For example, it often becomes necessary, in the performance of a PCI, to exchange one indwelling catheter for another catheter. In order to maintain a guide wire in position while withdrawing the catheter, the guide wire must be gripped at its proximal end to prevent it from being pulled out of the blood vessel with the catheter. For example, a PTCA catheter, which may typically be on the order of 135 centimeters long, is longer than the proximal portion of the standard guide wire that protrudes out of patient. Therefore, exchanging an over-the-wire PTCA catheter requires an exchange guide wire of about 300 centimeters long, whereas a standard guide wire is about 165 centimeters long.

In one type of over-the-wire catheter exchange, the standard length guide wire first is removed from the lumen of the indwelling catheter. Then, a longer exchange guide wire is passed through the catheter to replace the original wire. Next, while holding the exchange guide wire by its proximal end to control its position in the patient, the catheter is withdrawn proximally from the blood vessel over the exchange guide wire. After the first catheter has been removed, the next OTW catheter is threaded onto the proximal end of the exchange guide wire and is advanced along the exchange guide wire, through the guiding catheter, and into the patient's blood vessels until the distal end of the catheter is at the desired location. The exchange guide wire may be left in place or it may be exchanged for a shorter, conventional-length guide wire. In an alternative type of catheter exchange procedure, the length of the initial guide wire may be extended by way of a guide wire extension apparatus. Regardless of which exchange process is used, the very long exchange guide wire is awkward to handle, thus requiring at least two operators to perform the procedure.

Catheter designs have been developed in an attempt to eliminate the need for guide wire extensions or exchange guide wires. One such catheter design is the rapid exchange (RX) type catheter. Catheters of this type are formed so that the guide wire is located outside of the catheter except for a short guide wire lumen that extends within only a comparatively short distal segment of the catheter. The rapid exchange catheter's proximal exit port for the guide wire is typically located about 5 cm (2.0 in) to 30 cm (11.8 in) proximal to the catheter's distal end. In use, the guide wire is placed initially in the patient's vascular system. The distal segment of the RX catheter then is threaded onto the wire. The catheter can be advanced alongside the guide wire with its distal segment being attached to and guided along the guide wire. The RX catheter can be removed and exchanged for another RX catheter without the use of a very long exchange guide wire and without requiring withdrawal of the initially placed guide wire.

Although an RX catheter system may avoid the requirement for using a very long exchange wire, it presents several difficulties. First, without a full-length guide wire lumen, the proximal shaft of an RX catheter lacks an OTW catheter's coaxial interrelationship with the guide wire, which provides optimal transmission of force to push the distal end of the catheter through tight stenoses and/or tortuous blood vessels. FIGS. 1A and 2A illustrate guiding catheter 5, a shaft segment of OTW catheter 10 extending there through, and guide wire 15 disposed within guide wire lumen 17 in the common construction of coaxial tubes. The nested tubes result in an inner guide wire lumen 17 and an annular inflation lumen 19 formed between the tubes. The coaxial interrelationship with guide wire 15 provides an optimal transmission of force along the catheter length. In FIGS. 1B and 2B, inflation lumen 19' extends parallel to guide wire lumen 17' in a side-by-side arrangement. Although guide wire lumen 17' and guide wire 15' are located off-center in catheter 10', guide wire 15' is confined within catheter 10' throughout its length. Even if catheter 10' begins to buckle slightly when the distal tip of the catheter is being forced through a tight stenosis, there is very little misalignment with guide wire 15', such that most of the push force is transmitted to the distal tip. Therefore, despite their disadvantages during catheter exchange procedures, OTW catheters remain popular in the United States, due in part to the coaxial alignment between the catheter shaft and the guide wire, and the resulting excellent pushability of the device.

While improvements to RX catheters have incorporated stiff, metal proximal shafts and axial overlap between the shaft and the guide wire lumen to overcome the deficiencies discussed above, such RX catheters still are not optimal. FIG. 3 depicts prior art RX catheter 20 incorporating such a reinforced shaft 21, disposed over guide wire 15 within guiding catheter 5. However, even with continuous column support of the proximal shaft, the non-aligned or offset arrangement of guide wire 15 and shaft 21 of catheter 20, as illustrated in FIG. 4, can cause shaft buckling within the guiding catheter, as illustrated generally in FIG. 3, especially when the distal tip of the catheter is being forced through a tight stenosis. Such a non-coaxial misalignment causes displacement of push forces and an associated resistance to catheter advancement, especially in the region of proximal guide wire port 22.

A second difficulty associated with RX catheters is that it is not possible to exchange guide wires in an indwelling RX catheter, as can be done advantageously with OTW catheters. A guide wire can be withdrawn, sometimes unintentionally, from the proximal guide wire port, thus derailing an indwelling RX catheter. However, neither the first guide wire, nor a replacement guide wire, can be directed back into the catheter's proximal guide wire port, which is hidden remotely in the guiding catheter within the patient. FIG. 5 illustrates the problem of blindly steering the tip of guide wire 15 within guiding catheter 5 in an attempt to find and engage proximal guide wire port 22 of RX catheter 20.

A third difficulty associated with RX catheters is that, if the guide wire lumen is so short that the proximal guide wire port exits from the distal end of the guiding catheter, then the guide wire will be exposed. Such an RX device presents a risk of what is called the "cheese cutter effect," which is damage to the delicate inner surface of a curved artery from straightening tension applied to the exposed guide wire during push-pull maneuvers to advance the catheter. The short-lumen RX device also presents an increased risk of guide wire entanglement in those procedures where multiple guide wires are used, because the guide wires are exposed within the blood vessel. Furthermore, the exposed, unprotected portion of the guide wire can become kinked or tangled within the patient's vessel, adding complications to the procedure.

A fourth difficulty associated with RX catheters is encountered at the proximal end of the catheter system. There, the RX catheter and the guide wire extend from the guiding catheter side-by-side, making it awkward to seal the system against blood loss during manipulation of the components. The sealing, or "anti-backbleed" function is typically accomplished with a "Tuohy-Borst" fitting that has a manually adjustable gasket with a round center hole that does not conform well to the side-by-side arrangement of a catheter shaft and guide wire. A final difficulty associated with RX catheters is that the lack of a full-length guide wire lumen deprives the clinician of an additional lumen that may be used for other purposes, such as pressure measurement, injection of contrast dye distal to the stenosis, or infusing a drug.

A catheter designed to eliminate the need for guide wire extensions or exchange wires is disclosed in U.S. Pat. No. 4,988,356 (Crittenden et al.). This "zipper-type" catheter includes a catheter shaft having a cut that extends longitudinally between the proximal end and the distal end of the catheter and that extends radially from the catheter shaft outer surface to the guide wire lumen. A guide member slidably coupled to the catheter shaft functions to open the cut such that the guide wire may extend transversely into or out of the cut at any location along its length. By moving the guide member, the effective over-the-wire length of the zipper-type catheter is adjustable.

When using the zipper-type catheter, the guide wire is maneuvered through the patient's vascular system such that the distal end of the guide wire is positioned across the treatment site. With the guide member positioned near the distal end of the catheter, the proximal end of the guide wire is threaded into the guide wire lumen opening at the distal end of the catheter and through the guide member such that the proximal end of the guide wire protrudes out the proximal end of the guide member. By securing the guide member and the proximal end of the guide wire in a fixed position, the catheter may then be transported over the guide wire by advancing the catheter toward the guide member. In doing so, the catheter advances through the guide member such that the guide wire lumen envelops the guide wire as the catheter is advanced into the patient's vasculature. In a PTCA embodiment, the zipper-type catheter may be advanced over the guide wire in this manner until the distal end of the catheter having the dilatation balloon is positioned within the stenosis and essentially the entire length of the guide wire is encompassed within the guide wire lumen.

Furthermore, the indwelling zipper-type catheter may be exchanged with another catheter by reversing the operation described above. To this end, the indwelling catheter may be removed by withdrawing the proximal end of the catheter from the patient while holding the proximal end of the guide wire and the guide member in a fixed position. When the catheter has been withdrawn to the point where the distal end of the cut has reached the guide member, the distal portion of the catheter over the guide wire is of a sufficiently short length that the catheter may be drawn over the proximal end of the guide wire without releasing control of the guide wire or disturbing its position within the patient. After the catheter has been removed, another zipper-type catheter may be threaded onto the guide wire and advanced over the guide wire in the same manner described above with regard to the zipper-type catheter. The zipper-type catheter not only permits catheter exchange without the use of the very long exchange guide wire and without requiring withdrawal of the initially placed guide wire, but it also overcomes many of the other difficulties discussed in association with RX catheters.

Despite these advantages, original zipper-type catheters in accordance with the '356 patent had difficulties related to movement of the guide wire through the guide member. As disclosed in the '356 patent, the use of a hypodermic tubing member to direct a guide wire into and out of the guide wire lumen was found to be effective while the guide wire was stationary within the guide member, and while the catheter was translocated there through. However, if the guide wire were to be withdrawn through the guide member, the hypodermic tubing member would often scrape pieces of a lubricious coating from the guide wire. The resulting shavings, designated generally as 16 in FIG. 6, would become jammed in the annular space between the guide wire 15 and the hypodermic tubing member 26, preventing further movement of the guide wire.

In a more significant problem with the original zipper-type catheter, it could fail to adequately contain the guide wire within the guide wire lumen during normal operation. In particular, as the catheter was advanced over the guide wire, the catheter could bend or buckle such that the guide wire could protrude from the catheter shaft. If the guide wire protruded from the catheter shaft, it could subsequently become pinched, and the distal end of the guide wire could be pulled out of or pushed beyond the treatment site, thus complicating the procedure and requiring repositioning within the patient's vasculature. Bending or buckling of a zipper-type catheter could also occur proximal to the guide member, where the guide wire is absent from the guide wire lumen. It is among the general objects of the invention to provide an improved device that overcomes the foregoing difficulties.

SUMMARY OF THE INVENTION

The present invention is a catheter and guide wire exchange system comprising an elongate flexible catheter shaft having proximal and distal ends and first and second lumens extending there through, the first lumen being open at the shaft distal end and being sized and shaped to slidably receive a guide wire. A guide member is mounted on the catheter shaft and is received in a guide way formed from a longitudinal cut in the catheter shaft to enable transverse access to the first lumen through the shaft. The guide way extends along a major portion of the length of the shaft from a location adjacent the proximal end of the catheter to a location proximal of the shaft distal end. An elongate stiffening member is disposed within the second lumen from the shaft proximal end to a location adjacent the guide way distal end, and a balloon is mounted about shaft distal segment, the balloon being in fluid communication with the second lumen. The guide member has a catheter passageway extending there through for slidably receiving the catheter shaft and a guide wire passageway for slidably receiving the guide wire. The guide wire passageway intersects the catheter passageway for merging the guide wire and the catheter by guiding the guide wire transversely through the guide way in the catheter and into the first lumen. Conversely, the guide member can be used for separating the guide wire and catheter by guiding the guide wire transversely out of the first lumen through the guide way.

BRIEF DESCRIPTION OF THE DRAWINGS

These and other features, aspects and advantages of the present invention will become better understood with reference to the following description, appended claims, and accompanying drawings where:

FIG. 3 is a longitudinal sectional illustration of a section of a prior art rapid exchange catheter and guide wire system;

FIG. 4 is a transverse sectional illustration of a prior art rapid exchange catheter and guide wire system, taken along the line 4—4 of FIG. 3;

FIG. 5 is partial longitudinal sectional illustration of a section of a prior art rapid exchange catheter and guide wire system, shown within a guiding catheter;

FIG. 6 is a partial longitudinal sectional illustration of a section of a prior art zipper-type catheter and guide wire system;

FIG. 7 is an illustration of the catheter, guide wire and guide member of the present invention in an assembled configuration;

FIG. 8 is a transverse sectional illustration of the catheter and guide wire as seen along the line 8—8 of FIG. 7;

FIG. 9 is a transverse sectional illustration of the catheter, guide wire and guide member as seen along the line 9—9 of FIG. 7;

FIG. 10 is a transverse sectional illustration of the catheter, guide member and guide wire as seen along the line 10—10 of FIG. 7;

FIG. 11A is a transverse sectional illustration of the catheter and guide wire as seen along the line 11—11 of FIG. 7;

FIG. 11B is an alternative embodiment of the transverse sectional illustration of FIG. 11A shown as a multilumen arrangement;

FIG. 12 is an enlarged longitudinal sectional view of the guide member as seen along the line 12—12 in FIG. 7;

Figure 1A:
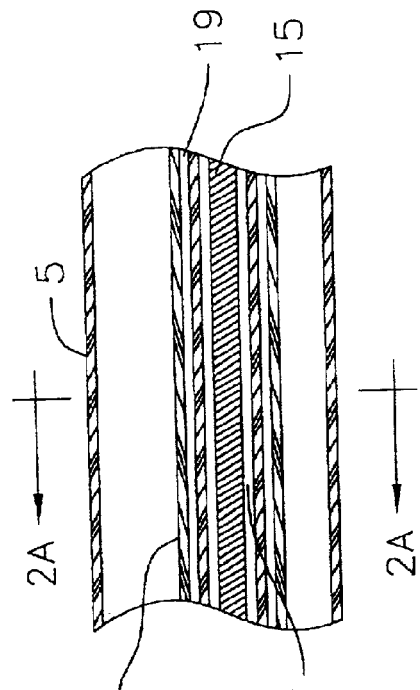
FIG. 1A is a longitudinal sectional illustration of a section of a prior art coaxial over-the-wire catheter and guide wire system.
Figure 1B:
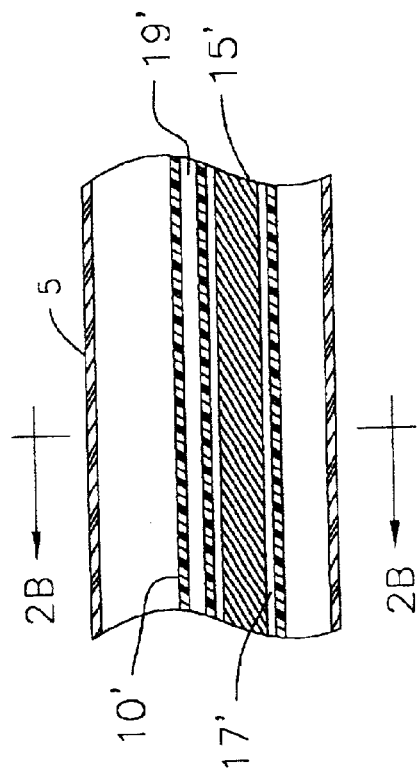
FIG. 1B is a longitudinal sectional illustration of a section of a prior art multilumen over-the-wire catheter and guide wire system.
Figure 2A:
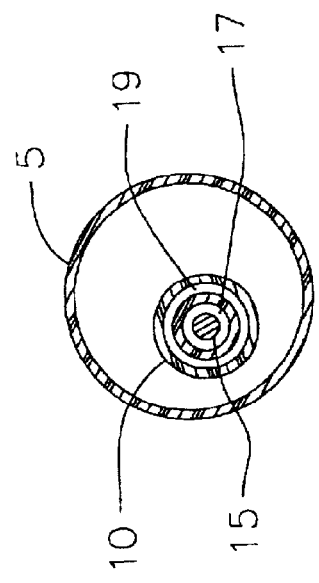
FIG. 2A is a transverse sectional illustration of a coaxial prior art over-the-wire catheter and guide wire system, taken along the line 2A—2A of FIG. 1A.
Figure 2B:
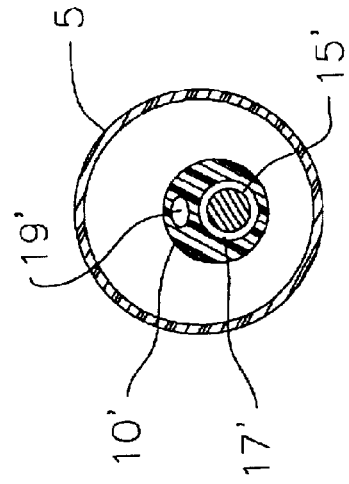
FIG. 2B is a transverse sectional illustration of a multi-lumen prior art over-the-wire catheter and guide wire system, taken along the line 2B—2B of FIG. 1B.

The drawings are not to scale.

DETAILED DESCRIPTION OF THE INVENTION

As shown in FIG. 7, the invention includes a catheter, indicated generally by the reference character 30, on which a guide member 32 is slidably mounted. Guide wire 15 is illustrated as extending through the guide member 32. Guide member 32 serves as a juncture in which the catheter 30 and guide wire 15 may be merged or separated so that the portion of guide wire 15 which extends proximally of guide member 32 (to the left as seen in FIG. 7) is separated from catheter 30 and the portion of guide wire 15 which is located distally of guide member 32 (to the right as seen in FIG. 7) is contained and housed within catheter 30 except for distal end 36 of guide wire 15 which may protrude distally out of distal end 38 of catheter 30.

Catheter 30 includes an elongate, flexible, cylindrical main body, which may be formed from an extruded plastic material such as, for example, polyethylene or polyethylene block amide (PEBA) copolymer. In the embodiment shown in FIG. 7, catheter 30 is a delivery catheter, such as for PTCA or stent delivery, having balloon 40 mounted around the catheter body near the distal end 38 of catheter 30. Balloon 40 may be inflated and deflated through inflation lumen 42 formed through the body of the catheter 30. Inflation lumen 42 extends from the proximal end of catheter 30, where it communicates with fitting 44 and extends the length of catheter 30, terminating in communication with the interior of balloon 40. Fitting 44 may be connected to a suitable source of pressurized fluid or a partial vacuum (not shown) to inflate or deflate balloon 40. Catheter 30 includes another lumen, indicated at 46, which is intended to receive guide wire 15. Guide wire lumen 46 may extend the full length of catheter 30, terminating at distal opening 38 and proximal fitting 44.

In accordance with the invention, the body of catheter 30 is formed with longitudinal guide way 48 which, when catheter 30 is viewed in cross-section, as in FIG. 8, may be considered as defining a pair of flaps 50 which normally close together at guide way 48 to define enclosed guide wire lumen 46. Guide wire lumen 46 may be circular in cross-section or may be non-circular; in either case, the cross-sectional dimensions of guide wire lumen 46 are greater than the cross-sectional dimension of guide wire 15 to permit relative longitudinal movement between guide wire 15 and catheter 30. Inflation lumen 42 encompasses elongate stiffening member 43, which causes the shaft of catheter 30 to have greater bending stiffness than guide wire 15. Stiffening member 43 extends at least through the length of catheter 30 that includes guide way 48, thus preventing the shaft from bending such that guide way 48 could buckle allowing guide wire 15 to protrude from the catheter shaft, as discussed earlier with respect to the original zipper-type catheter.

The proximal end of guide way 48 may terminate at or near fitting 44. In the embodiment shown in FIGS. 7 and 12, distal end 52 of guide way 48 terminates short of distal end 38 of catheter 30, thereby leaving distal segment 34 of catheter 30 in which guide wire lumen 46 is defined by a continuous surrounding wall 49 as shown in FIG. 11A. Adjacent guide way distal end 52, the shaft of catheter 30 may transform from the more proximal side-by-side arrangement of lumens to the more distal coaxial arrangement, as will be understood by those of skill in the art. Distal segment 34 preferably comprises a coaxial arrangement of two tubes, as shown in FIG. 11A with inner tube wall 49 communicating with and surrounding an extension of guide wire lumen 46. The outer tube 51 encompasses the inner tube, forming an annular lumen that extends inflation lumen 42 from the region of guide way distal end 52 to balloon 40. Optionally, the distal segment 34 may comprise a multilumen arrangement of the inflation lumen 42 and guide wire lumen 46 as shown in FIG. 11B.

Guide member 32 has proximal and distal ends, 54, 56, respectively, as shown in FIGS. 7 and 12. Catheter passageway 62 extends longitudinally in a generally straight line from guide member proximal end 54 to guide member distal end 56. Guide wire passageway 66 extends distally from its end 64, formed at guide member proximal end 54, to intersect catheter passageway 62 at a shallow angle, preferably in a coaxial relationship with guide wire lumen 46. Proximal spreader member 74 is formed in the body of guide member 32 and projects into catheter passageway 62, proximal to the intersection of passageways 62 and 66. Guide member also includes distal spreader member 76, located within guide member distal end 56. Distal spreader member 76 may serve to align catheter 30 within catheter passageway 62, and especially to line up guide way 48 with guide wire passageway 66. Distal spreader member 76 maybe disposed adjacent, alongside or spaced from the distal end of guide wire tube 68. As distinguished from proximal spreader member 74, distal spreader member 76 should not project into guide wire lumen 46, where it could interfere with guide wire 15, and longitudinal movement thereof.

Guide member 32 maybe molded from a suitable rigid plastic material, such as nylon or nylon based co-polymers that are preferably lubricious. Alternatively, guide member 32 maybe made of a suitable metal such as stainless steel or guide member 32 may have both metal components and plastic components. For ease in manufacturing, guide member 32 may be comprised of molded parts that snap-fit together to form the final configuration.

When catheter 30 and guide wire 15 both extend through guide member 32, they merge at the juncture of the passageways as shown in FIG. 12. Entering guide member proximal end 54, catheter 30 extends through catheter passageway 62, engaging spreader 74, which extends through guide way 48 in catheter 30 to spread flaps 50 apart as indicated in FIG. 9. Guide wire 15 may extend from end 64 through guide wire passageway 66 into catheter passageway 62, entering guide wire lumen 46 through spread-apart flaps 50. During advancement of catheter 30 through guide member 32, flaps 50 draw together under the influence of the inherent resiliency of the catheter body to close guide way 48, thus enclosing guide wire 15 within guide wire lumen 46. Guide wire 15 is contained within guide wire lumen 46 from the intersection of passageways 62, 66 within guide member 32 to distal opening 38. The shaft rigidity provided by stiffening member 43 allows catheter 30 to be pushed into guide member proximal end 54 without buckling, despite the lack of guide wire support in this region.

In an alternative maneuver, guide wire 15 maybe inserted or removed through guide wire passageway 66, while guide member 32 is held stationary with respect to catheter 30. In this fashion, guide wire 15 can be exchanged within catheter 30. In yet another type of manipulation, guide wire 15 and catheter 30 can be held relatively still while guide member 32 is translocated, thus unzipping and zipping guide wire 15 and catheter 30 transversely apart or together, depending on which direction guide member 32 is moved. In use, guide member 32 may be secured to a Touhy-Borst or Y-adapter and thus an outer section of guide member 32 may be configured to be received in such an adaptor.

To minimize the amount of material surrounding guide wire lumen 17 and inflation lumen 19, at least the shaft portion of catheter 30 comprising guide way 48 is generally oval in cross-sectional shape, as illustrated in FIGS. 8, 9 and 10. One advantage of such a catheter shape is that the small perimeter, and the correspondingly small area of the cross-section will maximize the surrounding annular space when catheter 30 lies within guiding catheter 5. An additional advantage of the oval cross-sectional shape is that catheter 30 will tend to align itself with catheter passageway 62, which has a matching oval cross-section, as shown in FIGS. 9 and 10. However, proximal shaft section 35 and catheter passageway 62 may also be generally circular. FIG. 11A illustrates distal section 34 of catheter 30 as having a round cross-sectional shape since it has a coaxial arrangement of the guide wire and inflation lumens. The distal section of catheter could, optionally, have an oval cross section such as shown in 11B, regardless of whether or not there is a coaxial or multilumen arrangement of the guide wire and inflation lumens.

Figure 13:
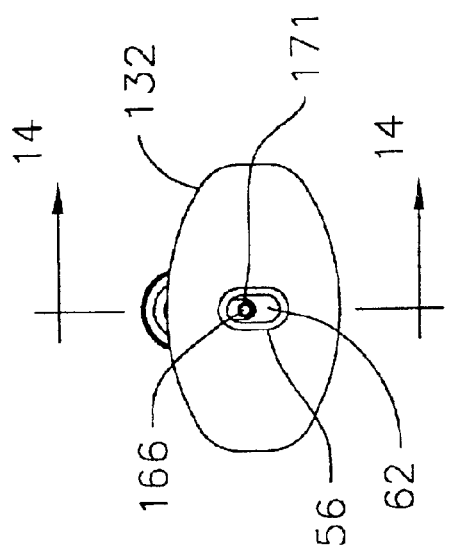
FIG. 13 is an end view of the distal end of one guide member embodiment in accordance with the invention.
Figure 14:
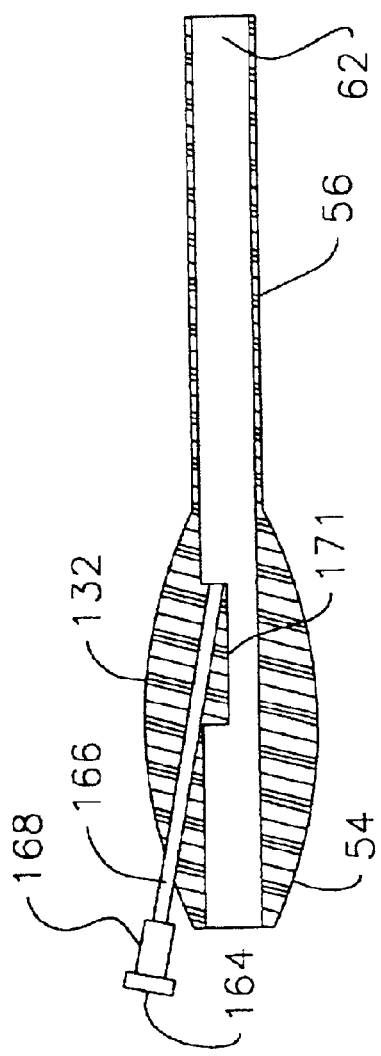
FIG. 14 is a longitudinal section illustration of the guide member as seen along the line 14—14 of FIG. 13.

FIGS. 13 and 14 depict guide member 132, a modified form including guide wire tube 168 having guide wire passageway 166 with end 164. Guide members 32 and 132 have similar elements, which will be identified with the same reference numerals throughout the description of the invention. Guide wire tube 168 may be formed of metal hypotubing or a strong, thin-walled polymer, such as thermoset polyimide (PI) tubing or other comparable material. End 164 maybe an over-molded fitting that is funnel-shaped to aid insertion of a curved tip of guide wire 15. Guide wire tube 168 may be fixed or slidably disposed in guide member 132. When it is inserted in guide member 132, guide wire tube 168 extends into catheter passageway 62 and through guide way 48 into guide wire lumen 46 of catheter 30. In this mode, guide wire tube 168 holds flaps 50 from interfering with "front-loading" insertion of guide wire 15 through passageway 166 into guide wire lumen 46. During "back-loading" operation, wherein guide wire 15 is inserted into guide wire lumen 46 through distal end 38, guide wire tube 168 can capture the proximal end of guide wire 15 and direct it into passageway 166. Guide wire passageway 166 may have a scoop-shaped or keel portion 171 adapted to align catheter 30 within catheter passageway 62. After insertion of guide wire 15 into catheter 30, guide wire tube 168 can be withdrawn and/or removed from guide member 132 to minimize friction as flaps 50 slide past guide wire 15 at the intersection of passageways 62 and 166. Keel portion 171 further assists in maintaining flaps 50 open at the appropriate location for passage of guide wire 15.

Figure 15:
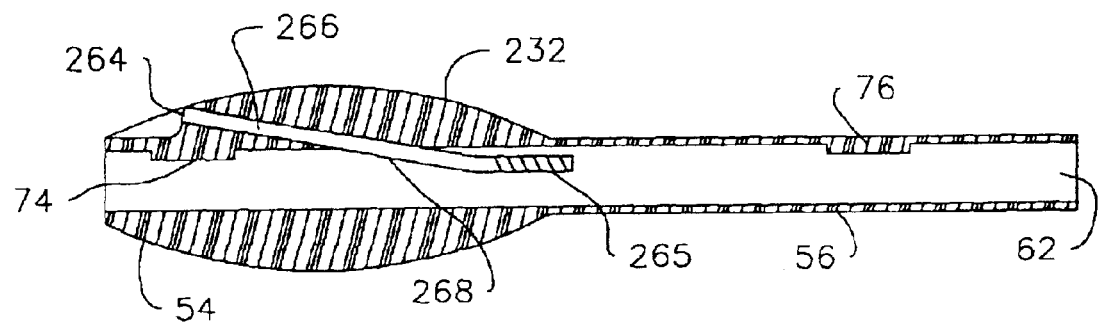
FIG. 15 illustrates a modified form of the guide member as illustrated in FIG. 12.

FIG. 15 depicts guide member 232, another modified form including guide wire tube 268 having guide wire passageway 266 with end 264. Guide wire tube 268 is fixedly mounted within guide member 232 and has a spirally cut distal end 265 that extends into catheter passageway 62 and within guide wire lumen 46. Spirally cut distal end 265 may be curved into alignment with guide wire lumen 46, as shown, and adds flexibility to guide wire tube 268, which is especially advantageous if it is made from metal hypotubing. Guide wire tube end 264 is located in a scallop-shaped recession formed in guide member proximal end 54 to aid insertion of a curved tip of guide wire 15.

Figure 16:
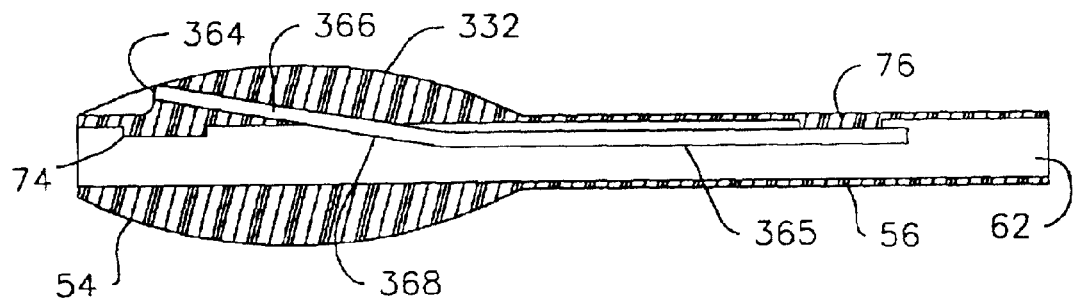
FIG. 16 illustrates another modified form of the guide member as illustrated in FIG. 12.

FIG. 16 illustrates guide member 332, another modified form including guide wire tube 368 having guide wire passageway 366 with end 364. Guide wire tube 368 is fixedly mounted within guide member 332 and extends into catheter passageway 62 with section 365 extending substantially into guide member distal end 56. The relatively increased length of guide wire tube 368 helps in alignment with guide wire lumen 46 and to avoid catching or dragging at its distal tip.

Figure 17:
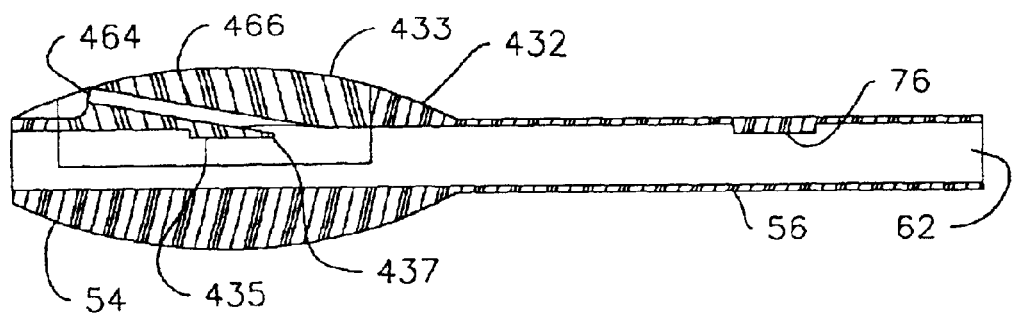
FIG. 17 illustrates another modified form of the guide member as illustrated in FIG. 12.

FIG. 17 depicts guide member 432, another modified form including insert member 433 having guide wire passageway 466 with end 464 and internal segment 435. Insert member 433 can be snap-fit into a cavity within guide member 432 such that internal segment 435 extends into catheter passageway 62. Internal segment 435 is shaped and sized to open guide way 48 and to fit within guide wire lumen 46. Internal segment 435 may have a scoop-shaped distal end 437 adapted to capture the proximal end of guide wire 15 during back-loading and direct it into passageway 466. Optionally, guide wire tube 168 may be fixed or slidably disposed within guide member 432, as discussed earlier, regarding guide member 132.

Figure 18:
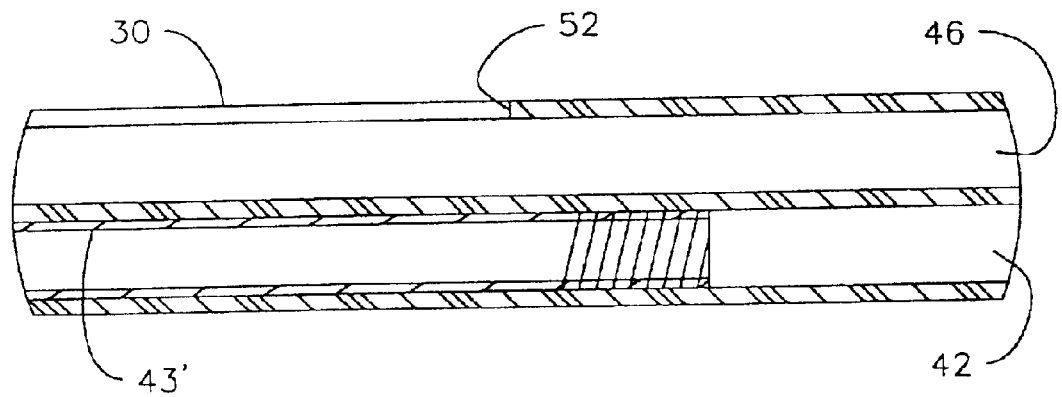
FIG. 18 is an enlarged view of a partially sectioned portion of the catheter in FIG. 7, showing the distal end of the stiffening member.
Figure 19:
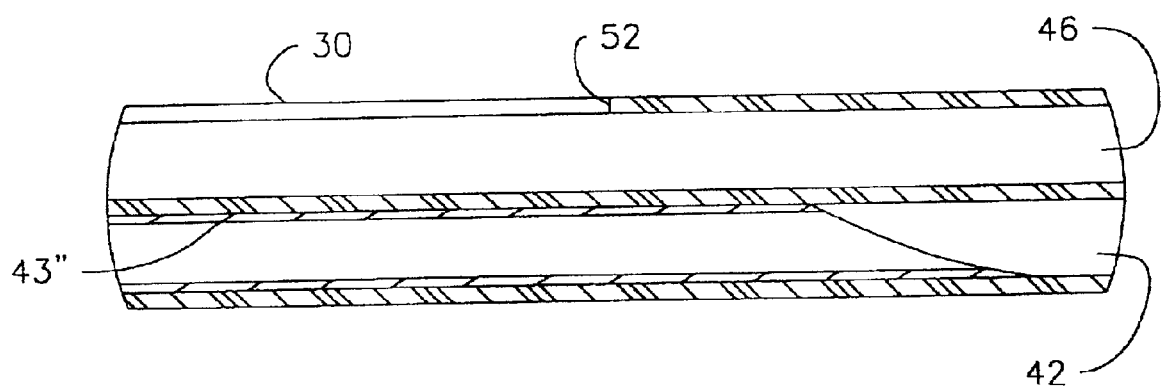
FIG. 19 illustrates a modified form of the distal end of the stiffening member, as shown in FIG. 18.
Figure 20:
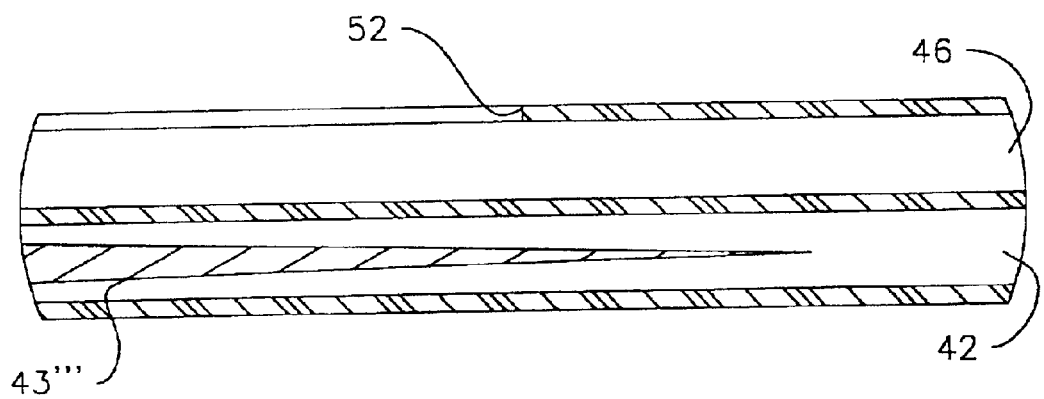
FIG. 20 illustrates another modified form of the distal end of the stiffening member, as shown in FIG. 18.

FIGS. 18–20 show stiffening member 43 in a transverse cross-sectional view. FIG. 18 illustrates a modified form, tubular stiffening member 43', wherein the distal end is spirally cut to provide more gradual transition in flexibility from the stiffened portion to the unstiffened portion of catheter 30. FIG. 19 illustrates another modified form, tubular stiffening member 43", wherein the distal end is skived, or cut at an angle to accomplish a gradual transition in flexibility similar to that provided by spirally-cut stiffening member 43'. Additionally, the helically spiral cut stiffening member 43" may also have a skived distal end. FIG. 20 illustrates another modified form, mandrel-type stiffening member 43''', which has a tapered distal end, and is fitted into inflation lumen 42, leaving sufficient annular space for fluid flow. While the stiffening member is shown as a component within the catheter shaft, a reinforced catheter wall is also contemplated if it provides sufficient support.

Figure 21:
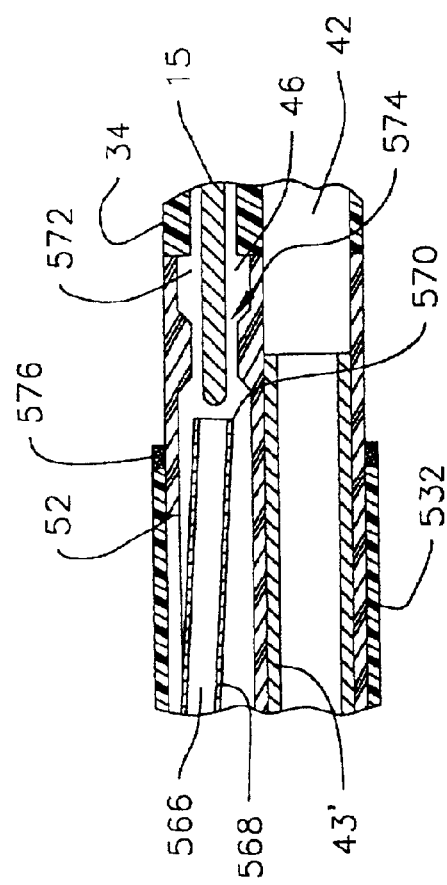
FIG. 21 is another enlarged view of a partially sectioned portion of the catheter in FIG. 7, showing an optional modification to the catheter shaft.

FIG. 21 depicts a transverse section of catheter 30 in the region of guide way distal end 52 with an optional modification to the shaft of catheter 30. In the "back-loading" operation described earlier, guide wire 15 can be inserted into and threaded proximally through guide wire lumen 46 until guide wire tube 568 captures the proximal end of guide wire 15 and directs it into passageway 566. This procedure is typically performed while guide member 532 is positioned adjacent guide way distal end 52, to temporarily minimize the effective over-the-wire length of guide wire lumen 46. Guide wire tube distal end 570 is positioned to be coaxial with guide wire lumen 46. However, the catheter may be furthered modified to assist in aligning guide wire tube 568 and the proximal end of guide wire 15 in order to complete the "back-loading" operation, especially if there is a difference in the guide wire lumen diameter at the transition between distal shaft section 34 and proximal shaft section 35, as shown generally at 572 in FIG. 21. Localized narrowing 574 can be formed in guide wire lumen 46 adjacent guide way distal end 52, to aid in aligning guide wire tube distal end 570 and the proximal end of guide wire 15 during "back-loading". Localized narrowing 574 can be molded into the shaft of catheter 30 using a short length of heat-shrink tubing and temporary support mandrels in guide wire lumen 46 and inflation lumen 42. This localized narrowing 574 cooperates with the diameter transition at 572 to further aid in aligning the guide wire with the guide wire tube. Although the narrowing is shown positioned distal to guide way distal end 52, it could, alternatively, be positioned proximal to guide way distal end 52, but distal to stop 576. Stop 576 is an optional feature that consists of a raised area on the outer surface of proximal shaft 35 adjacent its distal end. The raised area is greater in diameter than catheter passageway 62 and thus prevents guide member 32 from traveling past the proximal catheter shaft 35 and past the guide way distal end 52. Stop 576 may encircle the catheter shaft or it may consist of selectively raised areas on the catheter shaft.

In examples where the invention incorporates tubular stiffening members 43, 43' or 43", it is advantageous to fit the tubular member tightly within inflation lumen 42, such that all of the inflation/deflation fluid will flow through the lumen of the tubular member. The desired tight fit can be achieved by over-extruding the polymer shaft of catheter 30 onto tubular member 43, 43' or 43". The over-extrusion also improves the twist and kink resistance of the catheter shaft. In a first method of manufacturing, a substantial length of tubing can be fed through a wire-coating type of polymer extrusion head. Next, the substantial length of over-extruded tubing thus formed can be cut into approximately catheter-length pieces. In order to modify the distal ends of tubular member 43' or 43", a distal section of the over-extruded plastic shaft is cut away, exposing the tubing for alteration, such as spiral cutting or skiving. The last step in forming the shaft of catheter 30 is to add an uncut distal portion 34, as by adhesive or thermoplastic welding, using heat-shrink tubing and temporary support mandrels in guide wire lumen 46 and inflation lumen 42.

Alternatively, tubular members 43, 43' or 43", having a finished length and tip configuration, can be fed through a wire-coating type of polymer extrusion head, one-at-a-time. A distal section of the over-extruded plastic shaft is cut away and an uncut distal portion 34 can be added.

While the invention has been particularly shown and described with reference to the preferred embodiments thereof, it will be understood by those skilled in the art that various changes in form and detail may be made there in without departing from the spirit and scope of the invention.

We claim:

1. A catheter and guide wire exchange system comprising:
   An elongate flexible catheter shaft having proximal and distal ends and first and second lumens extending there through, the first lumen being open at the shaft distal end and being sized and shaped to slidably receive a guide wire;
   a longitudinal guide way formed in the catheter shaft to enable transverse access to the first lumen through the shaft, the guide way extending along a major portion off the length of the shaft from a location adjacent the shaft proximal end to a distal terminal end proximal of the shaft distal end, thereby defining an uncut distal segment of the shaft;
   an elongate stiffening member being disposed within the second lumen from the shaft proximal end to a location adjacent the guide way distal terminal end, the stiffening member increasingly flexible in the distal direction; and
   a balloon mounted about the shaft distal segment, the balloon being in fluid communication with the second lumen.

2. The catheter and guide wire exchange system of claim 1, and further including a fitting on the shaft proximal end wherein the fitting is in fluid communication with the second lumen.

3. The catheter and guide wire exchange system of claim 1, wherein the stiffening member is a metal wire.

4. The catheter and guide wire exchange system of claim 1, wherein the stiffening member is a metal tube.

5. The catheter and guide wire exchange system of claim 4, wherein the stiffening member distal end is skived.

6. The catheter and guide wire exchange system of claim 4, wherein the stiffening member distal end is spirally cut.

7. The catheter and guide wire exchange system of claim 4, wherein the catheter shalt has been formed by continually extruding thermoplastic over metal tubing, then cutting the extrudate into individual catheter lengths.

8. The catheter and guide wire exchange system of claim 4, wherein the catheter shaft has been formed by extruding thermoplastic over discrete lengths of metal tubing.

9. The catheter and guide wire exchange system of claim 1, wherein the catheter shaft has a proximal shaft section having a generally oval shaped perimeter.

10. The catheter and guide wire exchange of claim 1, wherein the balloon is a stent delivery balloon.

11. A catheter and guide wire exchange system comprising:
   an elongate flexible catheter shaft having proximal and distal ends and first and second lumens extending there through, the first lumen being open at the shaft distal end and being sized and shaped to slidably receive a guide wire;
   a longitudinal guide way formed in the catheter shaft to enable transverse access to the first lumen through the shaft, the guide way extending along a major portion of the length of the shaft from a location adjacent the shaft proximal end to a distal terminal end proximal of the shaft distal end, thereby defining an uncut distal segment of the shaft;
   an elongate stiffening member being disposed within the second lumen from the shaft proximal end to a location adjacent the guide way distal terminal end, the stiffening member increasingly flexible in the distal direction;
   a balloon mounted about shaft distal segment, the balloon being in fluid communication with the second lumen; and
   a guide member mounted on the catheter shaft and having a catheter passageway extending there through for slidably receiving the catheter shaft and a guide wire passageway for slidably receiving the guide wire, and which intersects the catheter passageway for merging the guide wire and the catheter by guiding the guide wire transversely through the guide way and into the first lumen and for separating the guide wire and catheter by guiding the guide wire transversely out of the first lumen through said guide way.

12. The catheter and guide wire exchange system of claim 11, wherein the guide member has at least one spreader member disposed within the catheter passageway and being adapted to open and to protrude through the guide way into the first lumen.

13. The catheter and guide wire exchange system of claim 12, wherein the at least one spreader member is located proximal of the intersection of the passageways.

14. The catheter and guide wire exchange system of claim 12, wherein the at least one spreader member is located distal of the intersection of the passageways.

15. The catheter and guide wire exchange system of claim 11, wherein the guide wire passageway extends through an insert member having an internal segment extending into the catheter passageway and being shaped and sized to open the guide way and to fit within the first lumen.

16. The catheter and guide wire exchange system of claim 15, wherein the insert member comprises hollow tubing.

17. The catheter and guide wire exchange system of claim 16, wherein the insert member is selectively removable from the guide member.

18. The catheter and guide wire exchange system of claim 16, wherein the insert member comprises metal tubing.

19. The catheter and guide wire exchange system of claim 18, wherein the metal tubing has a distal end that is spirally cut.

20. The catheter and guide wire exchange system of claim 16, wherein the insert member comprises polyimide tubing.

21. The catheter and guide wire exchange system of claim 20, wherein the polyimide tubing has a lubricious inner surface.

22. The catheter and guide wire exchange system of claim 15, wherein the internal segment comprises a scoop-shaped element adapted to receive and direct a guide wire proximal end through the guide wire passageway.

23. The catheter and guide wire exchange system of claim 11 wherein the balloon is a stent delivery balloon.

* * * * *

UNITED STATES PATENT AND TRADEMARK OFFICE
CERTIFICATE OF CORRECTION

| | |
|---|---|
| PATENT NO. | : 6,800,065 B2 |
| APPLICATION NO. | : 10/116234 |
| DATED | : October 5, 2004 |
| INVENTOR(S) | : Patrick J. Duane et al. |

It is certified that error appears in the above-identified patent and that said Letters Patent is hereby corrected as shown below:

Column 12, line 29, "catheter shalt" should be changed to -- catheter shaft --

Signed and Sealed this

Second Day of January, 2007

JON W. DUDAS
*Director of the United States Patent and Trademark Office*